(12) United States Patent
Buchbinder et al.

(10) Patent No.: US 9,522,859 B2
(45) Date of Patent: Dec. 20, 2016

(54) METHODS FOR RECOVERING IONIC LIQUID FINES FROM A PROCESS STREAM

(71) Applicant: UOP LLC, Des Plaines, IL (US)

(72) Inventors: Avram M. Buchbinder, Chicago, IL (US); Kurt Detrick, Glen Ellyn, IL (US); Trung Pham, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 214 days.

(21) Appl. No.: 14/567,877

(22) Filed: Dec. 11, 2014

(65) Prior Publication Data

US 2016/0168055 A1 Jun. 16, 2016

(51) Int. Cl.
| | | |
|---|---|---|
| C07C 7/00 | (2006.01) | |
| C07C 7/04 | (2006.01) | |
| B01D 3/14 | (2006.01) | |
| B01D 17/02 | (2006.01) | |

(52) U.S. Cl.
CPC .............. *C07C 7/005* (2013.01); *B01D 3/143* (2013.01); *B01D 17/0208* (2013.01); *C07C 7/04* (2013.01)

(58) Field of Classification Search
None
See application file for complete search history.

(56) References Cited

U.S. PATENT DOCUMENTS

| | | |
|---|---|---|
| 5,500,132 A | 3/1996 | Elmi |
| 6,858,770 B2 | 2/2005 | Smith, Jr. et al. |
| 8,067,656 B2 | 11/2011 | Luo et al. |
| 8,237,004 B2 | 8/2012 | Timken et al. |
| 9,328,296 B2 * | 5/2016 | Buchbinder ......... C10G 29/205 |
| 2011/0155640 A1 | 6/2011 | Timken et al. |
| 2012/0292507 A1* | 11/2012 | Morikawa ............ G01N 1/2813 250/307 |
| 2013/0066130 A1 | 3/2013 | Luo et al. |
| 2013/0066132 A1 | 3/2013 | Cleverdon et al. |
| 2013/0066133 A1 | 3/2013 | Cleverdon et al. |
| 2013/0243672 A1 | 9/2013 | Timken et al. |
| 2014/0018598 A1* | 1/2014 | Pfeiffer ............... B01D 17/045 585/818 |
| 2014/0171720 A1 | 6/2014 | Zhan et al. |

FOREIGN PATENT DOCUMENTS

JP 4542427 B2 9/2010

\* cited by examiner

*Primary Examiner* — Tam M Nguyen

(57) ABSTRACT

Methods of recovering droplets of ionic liquid catalyst from a process stream are described. The volume fraction of ionic liquid in the hydrocarbon is increased to cause the ionic liquid droplets to coalesce. One method incorporates various combinations of gravity separation zone(s) and fractionation zones. Another method involves using a combination of a flash vessel and a fractionation zone, as well as an optional gravity separation zone.

20 Claims, 6 Drawing Sheets

US 9,522,859 B2

METHODS FOR RECOVERING IONIC LIQUID FINES FROM A PROCESS STREAM

BACKGROUND OF THE INVENTION

Ionic liquids are essentially salts in a liquid state, and are described in U.S. Pat. Nos. 4,764,440, 5,104,840, and 5,824,832, for example. Ionic liquids typically melt below room temperature.

Ionic liquids have been used to catalyze a variety of hydrocarbon conversion processes, such as alkylation, isomerization, disproportionation, and the like. When ionic liquids are used to catalyze hydrocarbon conversion processes, the hydrocarbon feed and the ionic liquid catalyst are typically mixed with high shear to provide intimate contact. During the mixing, small droplets of ionic liquid become suspended in the immiscible phase, and some of these small droplets of ionic liquid remain entrained in the immiscible phase after conventional liquid-liquid phase separation by gravity. Because of the relatively high cost of ionic liquids, it is important to recover this entrained ionic liquid.

One method of recovering entrained ionic liquids is described in U.S. Pat. No. 8,067,656. The process involves coalescing ionic liquid droplets onto a coalescing material, coalescing the small droplets into larger droplets on the surface of the material, and capturing the coalesced droplets by settling to provide an ionic liquid layer. However, this method requires the use of a coalescing material.

Another method is described in U.S. application Ser. No. 14/229,462, entitled Process for Recovering Entrained Ionic Liquid from an Ionic Liquid Immiscible Phase, filed Mar. 28, 2014. The method involves contacting a hydrocarbon stream containing ionic liquid droplets with additional ionic liquid in order to increase the ionic liquid volume fraction and recover the ionic liquid droplets.

There is a need for additional methods of recovering entrained ionic liquids.

SUMMARY OF THE INVENTION

One aspect of the invention involves a method of recovering ionic liquid from a process stream. In one embodiment, the method includes separating the process stream comprising a mixture of hydrocarbons and ionic liquid into an ionic liquid phase and a hydrocarbon phase in a gravity separation zone, the hydrocarbon phase containing droplets of ionic liquid, and the hydrocarbon phase having a first volume fraction of ionic liquid. The hydrocarbon phase is fractionated into at least two hydrocarbon fractions, at least one of the hydrocarbon fractions containing the droplets of ionic liquid, the fraction containing the droplets of ionic liquid having a second volume fraction of ionic liquid, the second volume fraction being greater than the first volume fraction. At least a portion of the hydrocarbon fraction containing the droplets of ionic liquid is separated in a second separation zone into an ionic liquid stream and at least one hydrocarbon stream.

In another embodiment, the method includes flashing at least a portion of the process stream comprising a mixture of hydrocarbons and ionic liquid into a vapor phase comprising a first portion of at least one first hydrocarbon and a liquid phase comprising a second portion of the at least one first hydrocarbon, at least one second hydrocarbon, and the ionic liquid, and separating the liquid phase into an ionic liquid phase and a hydrocarbon phase in a flash vessel, wherein the flash vessel is at a pressure between a bubble point of the at least one first hydrocarbon and a bubble point of a at least one second hydrocarbon. The hydrocarbon phase is fractionated into at least two fractions.

DETAILED DESCRIPTION OF THE INVENTION

This invention utilizes increase in the ionic liquid to hydrocarbon volume fraction to coalesce ionic liquid droplets without using a coalescing material. Since the unreacted hydrocarbon needs to be separated from the product, this separation is utilized to increase the volume fraction of ionic liquid in the liquid phase. With unreacted hydrocarbon removed, the ionic liquid volume fraction in the remaining hydrocarbon is higher. Ionic liquid droplets increase their collision frequency and coalescence increases. The resulting larger ionic liquid droplets are separated by gravity or other methods.

In some embodiments, the process has the advantage of utilizing conditions in separation steps that are already being used in the hydrocarbon conversion process.

This process can be used to remove ionic liquid entrained in a hydrocarbon phase no matter where the process stream comes from. For example, the raffinate from an extraction process utilizing an ionic liquid could include entrained ionic liquid. Another possibility is the solvent and excess reagent used in the ionic liquid synthesis. Another source could be the solvent, excess regenerant, and converted regenerant in an ionic liquid regeneration process. Various hydrocarbon conversion processes will also generate entrained ionic liquid, including, but not limited to, alkylation, isomerization, oligomerization, disproportionation, reverse disproportionation, and the like.

The hydrocarbon feed used will depend on the process. For example, the alkylation feed could be isobutane and $C_3$-$C_5$ olefins. The feed for an isomerization process will typically be paraffins, kerosene or naphtha. The feed for a disproportionation process will typically be paraffins such as $C_4$-$C_7$ paraffins. The feed for a reverse disproportionation process will typically be paraffins such as $C_4$-$C_{16}$ paraffins. For ease of discussion, the process will be described for use in an alkylation process involving isobutane and butene.

Figure 1:
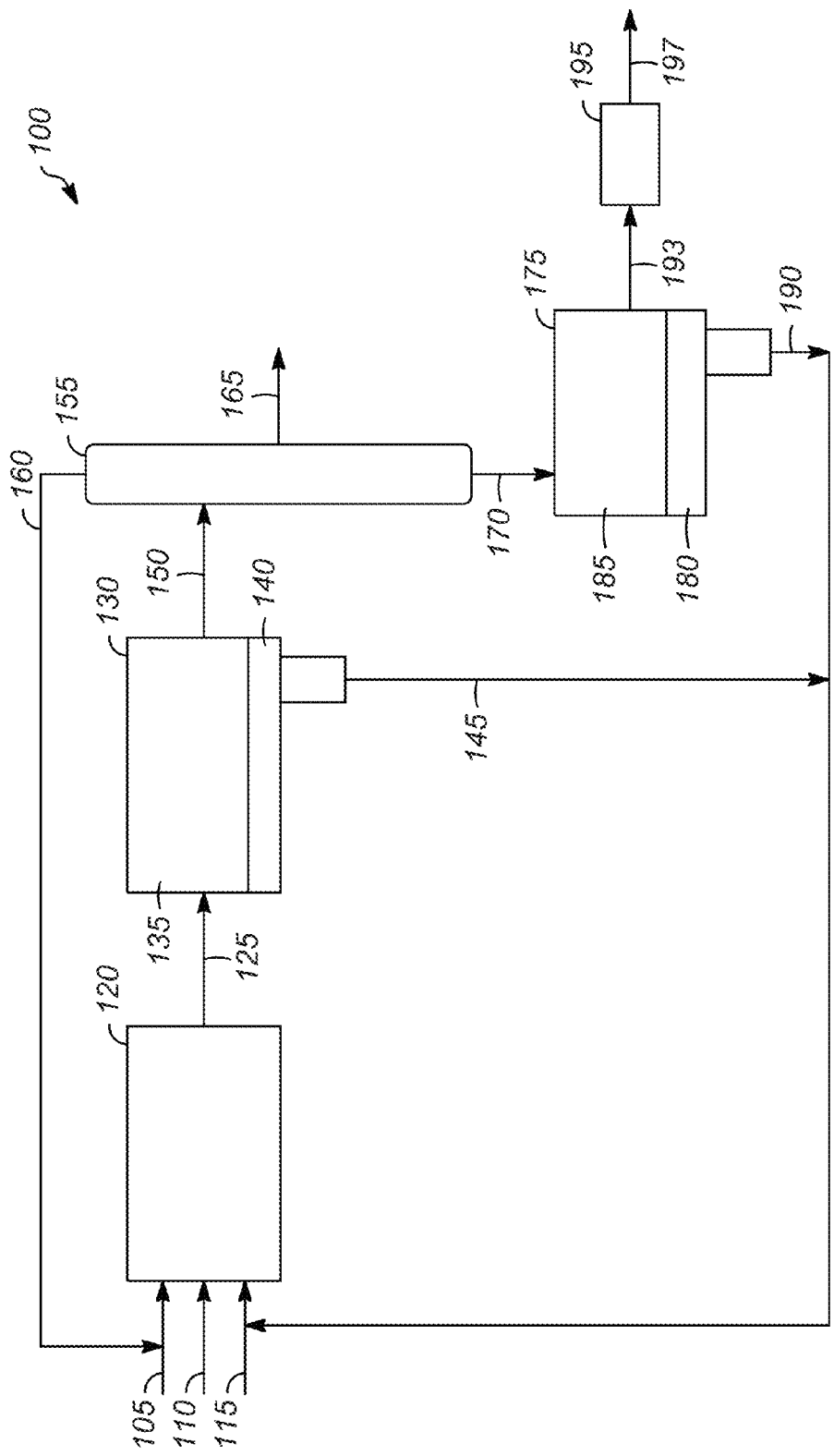
FIG. 1 illustrates one embodiment of a method for recovering entrained ionic liquid from an ionic liquid immiscible phase containing droplets of ionic liquid.

In the alkylation process 100 as illustrated in FIG. 1, a hydrocarbon feed 105, such as isobutane, an olefin feed 110, such as butene, and an ionic liquid catalyst 115 are fed into an alkylation reaction zone 120.

The ionic liquid can be any ionic liquid. There can be one or more ionic liquids. The ionic liquid comprises an organic cation and an anion. Suitable cations include, but are not limited to, nitrogen-containing cations and phosphorus-containing cations. Suitable organic cations include, but are not limited to:

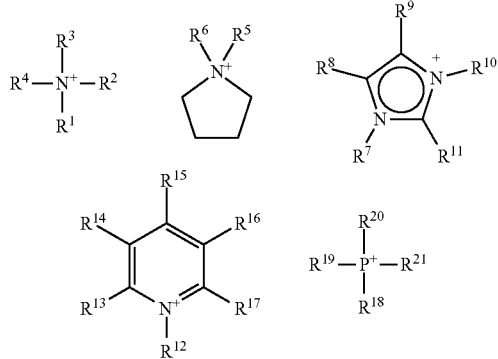

where $R^1$-$R^{21}$ are independently selected from $C_1$-$C_{20}$ hydrocarbons, $C_1$-$C_{20}$ hydrocarbon derivatives, halogens, and H. Suitable hydrocarbons and hydrocarbon derivatives include saturated and unsaturated hydrocarbons, halogen substituted and partially substituted hydrocarbons and mixtures thereof. $C_1$-$C_8$ hydrocarbons are particularly suitable. Lactamium based ionic liquids can also be used, such as those described in U.S. Pat. No. 8,709,236, U.S. application Ser. No. 14/271,308, entitled Synthesis of Lactam Based Ionic Liquids, filed May 6, 2014, and U.S. application Ser. No. 14/271,319, entitled Synthesis of N-Alkyl Lactam Based Ionic Liquids, filed May 6, 2014, each of which is incorporated herein by reference.

In some embodiments, the anion can be derived from halides, typically halometallates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br^-$). In some embodiments, the metal is aluminum, with the mole fraction of aluminum ranging from $0<Al<0.25$ in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $PF_6^-$, and $BF_4^-$. In other embodiments, other anions could be used.

The reaction mixture is subjected to high shear mixing in order to obtain good contact between the ionic liquid catalyst and the reactants. The high shear mixing generates an emulsion comprising ionic liquid, alkylate product, unreacted isobutane, and n-butane. The method of high sheer mixing is not important for this invention (could be impellers, nozzles, static mixers etc.).

The effluent 125 comprising the emulsion is fed to a gravity separation zone 130, such as a gravity settler. Because the ionic liquid is heavier than the hydrocarbons, the effluent separates into a lighter hydrocarbon phase 135 on top of a heavier ionic liquid phase 140. The majority of the ionic liquid settles into the ionic liquid phase 140 and is removed from the gravity separation zone 130 as ionic liquid stream 145. The residence time in the gravity settler is generally less than about 3 hr, or less than about 2.5 hr, or less than about 2 hr, or less than about 1.5 hr, or less than about 1 hr, or less than about 45 min, or less than about 30 min, or about 5 min to about 30 min.

Ionic liquid stream 145 can be recycled to the alkylation reaction zone 120. In some processes, at least a portion of the ionic liquid stream 145 could be sent to a regeneration zone (not shown) before being returned to the alkylation reaction zone 120. In other embodiments, at least a portion of the ionic liquid stream 145 could be removed from the process (not shown).

The lighter hydrocarbon phase 135 contains isobutane, n-butane, alkylate product, and small droplets of ionic liquid dispersed in the hydrocarbons that did not separate by gravity. The amount of ionic liquid droplets in the hydrocarbon phase after the gravity separation zone is typically on the order of about 250 ppm. The droplet size is typically less than about 50 μm.

Additional separation steps may take place on the hydrocarbon phase 135 following gravity separation, but are not necessary. Such additional separations may include, but are not limited to, coalescing with a coalescing material, or separation with centrifugal force.

A hydrocarbon stream 150 of the hydrocarbon phase 135 is sent to a fractionation column 155.

The operating pressure and the temperatures of the reboiler, the side stream draw, and the overhead of the fractionation column 155 are selected to provide the desired separation of the particular hydrocarbon components in the effluent. Additionally, the reboiler temperature can be selected so as not to thermally decompose the particular ionic liquid. If necessary, the pressure of the column can be adjusted downwards to allow operation of the reboiler at lower temperature. For example, when operating the fractionation column at a pressure in the range of about 965 kPa (g) (140 psig) to about 1310 kPa (g) (190 psig), the side draw for the n-butane would be in the range of about 82° C. (180° F.) to about 127° C. (260° F.), and the reboiler temperature would be in the range of about 149° C. (300° F.) to about 216° C. (420° F.).

The column overhead stream 160 contains primarily unreacted isobutane which is recycled to the alkylation reaction zone 120.

The side-draw stream 165 contains primarily n-butane. In some embodiments, the n-butane can be isomerized to isobutane and sent to the reaction zone. Alternatively, the n-butane can be recovered as a product.

The column bottoms stream 170 contains alkylate product and ionic liquid droplets that were not separated in the gravity separation zone 130. The column bottoms stream 170 is fed to a second separation zone 175. Second separation zone 175 can be any suitable type of separation zone including but not limited to, a gravity separator, electrostatic precipitator, coalescer, centrifugal separator, filter, scrubber, a zone for re-contacting with ionic liquid, extraction zones, and membrane separation zones.

Since the volume fraction of ionic liquid in the column bottoms stream 170 is significantly greater than the volume fraction of ionic liquid in the hydrocarbon stream 150 fed to the fractionation column 155 because of the removal of the isobutane and n-butane, at least a portion of the ionic liquid droplets coalesce and form an ionic liquid phase 180 under the lighter alkylate hydrocarbon phase 185. The recovered ionic liquid stream 190 from the second separation zone 175 can be recycled to the alkylation reaction zone 120. In some embodiments, all or a portion of the recovered ionic liquid stream 190 could be sent to a regeneration zone and/or a reactivation zone (not shown). The treated ionic liquid could then be recycled or sent to another process as desired.

A stream 193 of the lighter alkylate phase 185 can optionally be treated with a treater 195 to remove remaining the ionic liquid. However, such treatment results in ionic liquid loss, which is undesirable. Suitable treaters include, but are not limited to, glass, quartz, or ceramic material in the form of chips, fibers, or beads, as well as chloride treaters, silica gel, wool, solvent washes, and the like.

The treated alkylate 197 can be recovered and used for gasoline blending.

Figure 2:
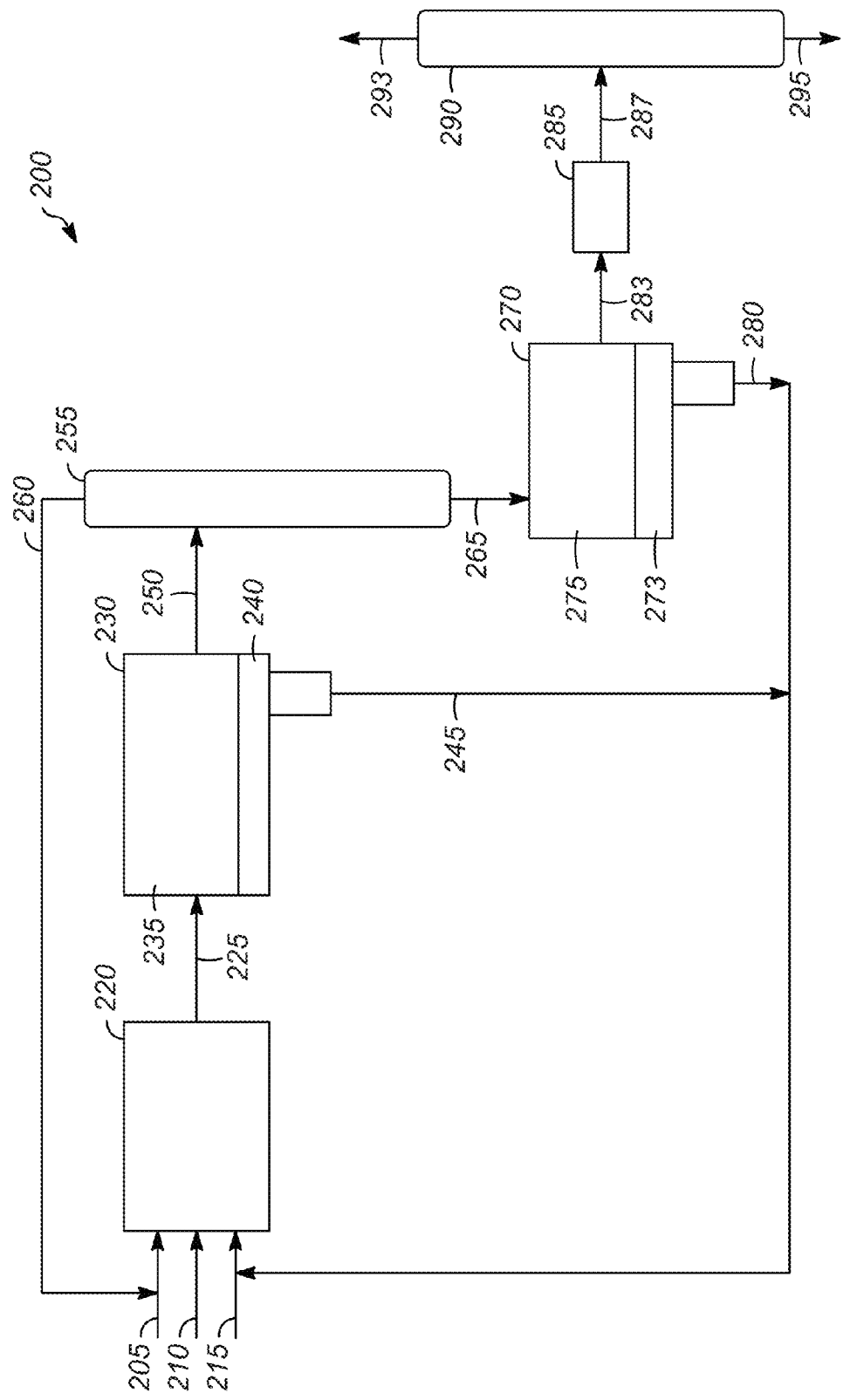
FIG. 2 illustrates another embodiment of a method for recovering entrained ionic liquid from an ionic liquid immiscible phase containing droplets of ionic liquid.

FIG. 2 illustrates another embodiment of the process 200. Some ionic liquids will not be stable at the reboiler temperatures used in the process shown in FIG. 1 while operating at a practical pressure. To solve this problem, rather than utilizing a single fractionation column to separate isobutane, n-butane, and alkylate, two fractionation columns are used.

A hydrocarbon feed 205, an olefin feed 210, and an ionic liquid catalyst 215 are fed into an alkylation reaction zone 220 for reaction. The effluent 225 is fed to a gravity separation zone 230, where is separates into a lighter hydrocarbon phase 235 on top of a heavier ionic liquid phase 240. The ionic liquid phase 240 is removed from the gravity separation zone 230 as ionic liquid stream 245 and can be recycled to the alkylation reaction zone 220.

A hydrocarbon stream 250 of the hydrocarbon phase 235 is sent to a first fractionation column 255. The first fractionation column 255 can be run with a cooler reboiler (compared to fractionation column 155 in the process 100 of FIG. 1) at about 104° C. (220° F.) to about 182° C. (360° F.) when operated at about 965 kPa (g) (140 psig) to about 1310 kPa (g) (190 psig). In this case, the column overhead stream 260 contains isobutane, there is no side-draw, and the column bottoms stream 265 contains alkylate, n-butane, and ionic liquid droplets.

The column bottoms stream 265 is sent to a second separation zone 270 where it is separated into an ionic liquid phase 273 and a hydrocarbon phase 275. The volume fraction of ionic liquid in column bottoms stream 265 is greater than the volume fraction of ionic liquid in the hydrocarbon stream 250.

A stream of ionic liquid 280 is recycled to the alkylation reaction zone 220.

The hydrocarbon phase 275 contains alkylate and n-butane. A stream 283 of the hydrocarbon phase 275 is fed to an optional treater 285. The treated stream 287 is sent to a second fractionation column 290 where the n-butane fraction 293 is separated from the alkylate fraction 295.

Figure 3:
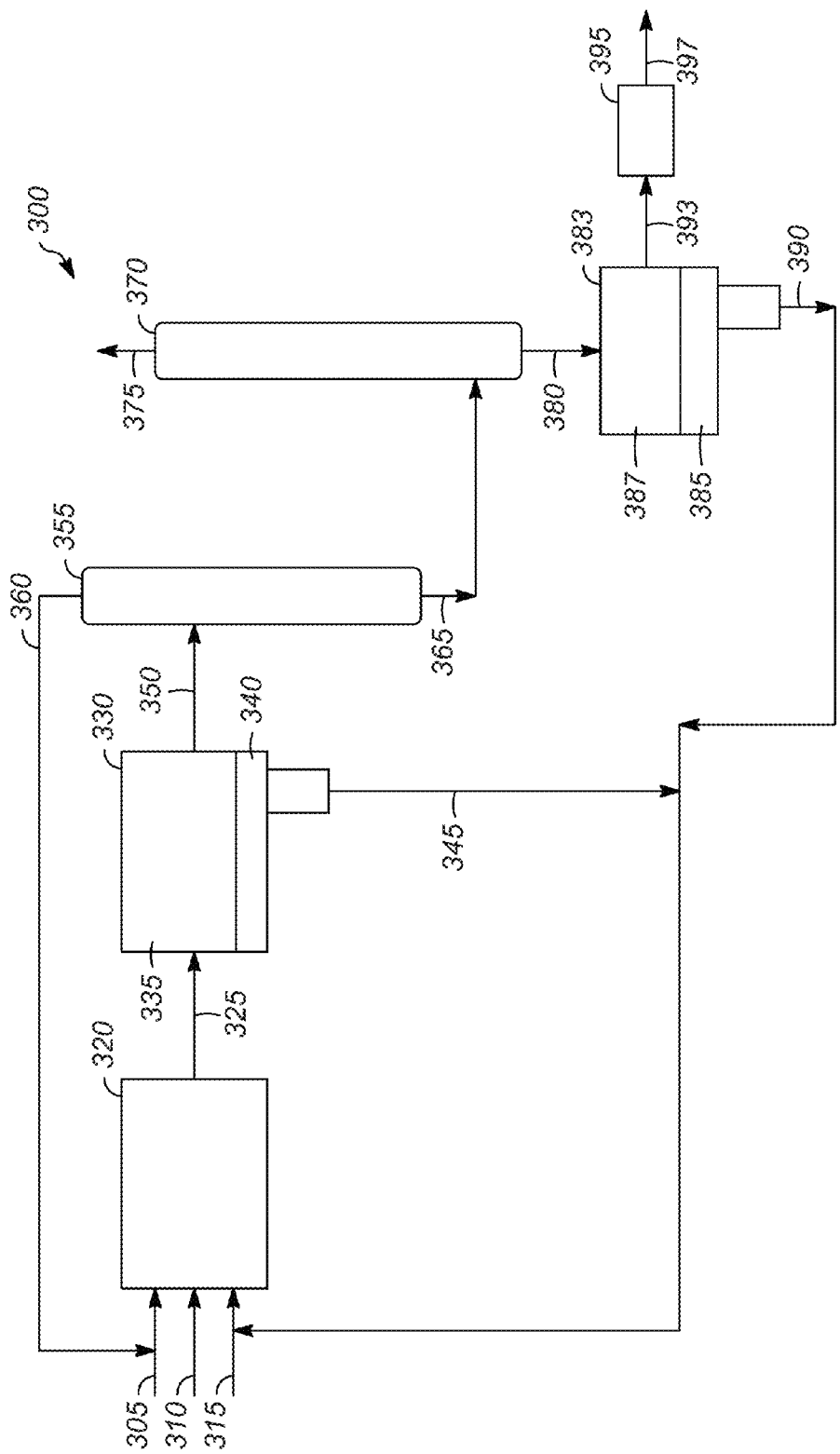
FIG. 3 illustrates still another embodiment of a method for recovering entrained ionic liquid from an ionic liquid immiscible phase containing droplets of ionic liquid.

FIG. 3 illustrates another embodiment of the process 300. A hydrocarbon feed 305, an olefin feed 310, and an ionic liquid catalyst 315 are fed into an alkylation reaction zone 320. The effluent 325 is fed to a gravity separation zone 330, where is separates into a lighter hydrocarbon phase 335 on top of a heavier ionic liquid phase 340. The ionic liquid phase 340 is removed from the gravity separation zone 330 as ionic liquid stream 345 and can be recycled to the alkylation reaction zone 320.

A hydrocarbon stream 350 of the hydrocarbon phase 335 is sent to a first fractionation column 355.

In this case, rather than placing the second separation zone 383 between the first fractionation column 355 and the second fractionation column 370, the reboiler for the first fractionation zone is run at a low temperature about 82° C. (180° F.) to about 138° C. (280° F.) and a pressure of about 965 kPa (g) (140 psig) to about 1310 kPa (g) (190 psig) with no side draw. The overhead stream 360 is isobutane, and the bottoms stream 365 contains alkylate, n-butane and ionic liquid fines. The bottoms stream 365 is sent to the second fractionation column 370 at a lower pressure, such as about 620 kPa (g) (90 psig) to about 965 kPa (g) (140 psig), which allows operation at low reboiler temperature, such as about 82° C. (180° F.) to about 138° C. (280° F.) (compared to fractionation column 290 in process 200 in FIG. 2). The n-butane is removed in the overhead stream 375, and the bottoms stream 380 is fed to the second separation zone 383. The volume fraction of ionic liquid in the bottoms stream 380 is greater than the volume fraction of ionic liquid in the hydrocarbon stream 350.

The bottoms stream 380 is separated into an ionic liquid phase 385 and a hydrocarbon phase 387. A stream 390 of the ionic liquid phase 385 is recycled to the alkylation reaction zone 320.

A stream 393 of the hydrocarbon phase 387 is sent to a treater 395. The treated alkylate stream 397 can be recovered and used for gasoline blending.

In this case, the product treater 395 is after the second separation zone 383. This has the advantage over the arrangement in FIG. 2 of removing n-butane in addition to isobutane in order to promote coalescence, and it may operate at lower temperature to prevent thermal degradation of the ionic liquid. However, it may require corrosion resistant metallurgy in the reboilers of both columns.

Figure 4:
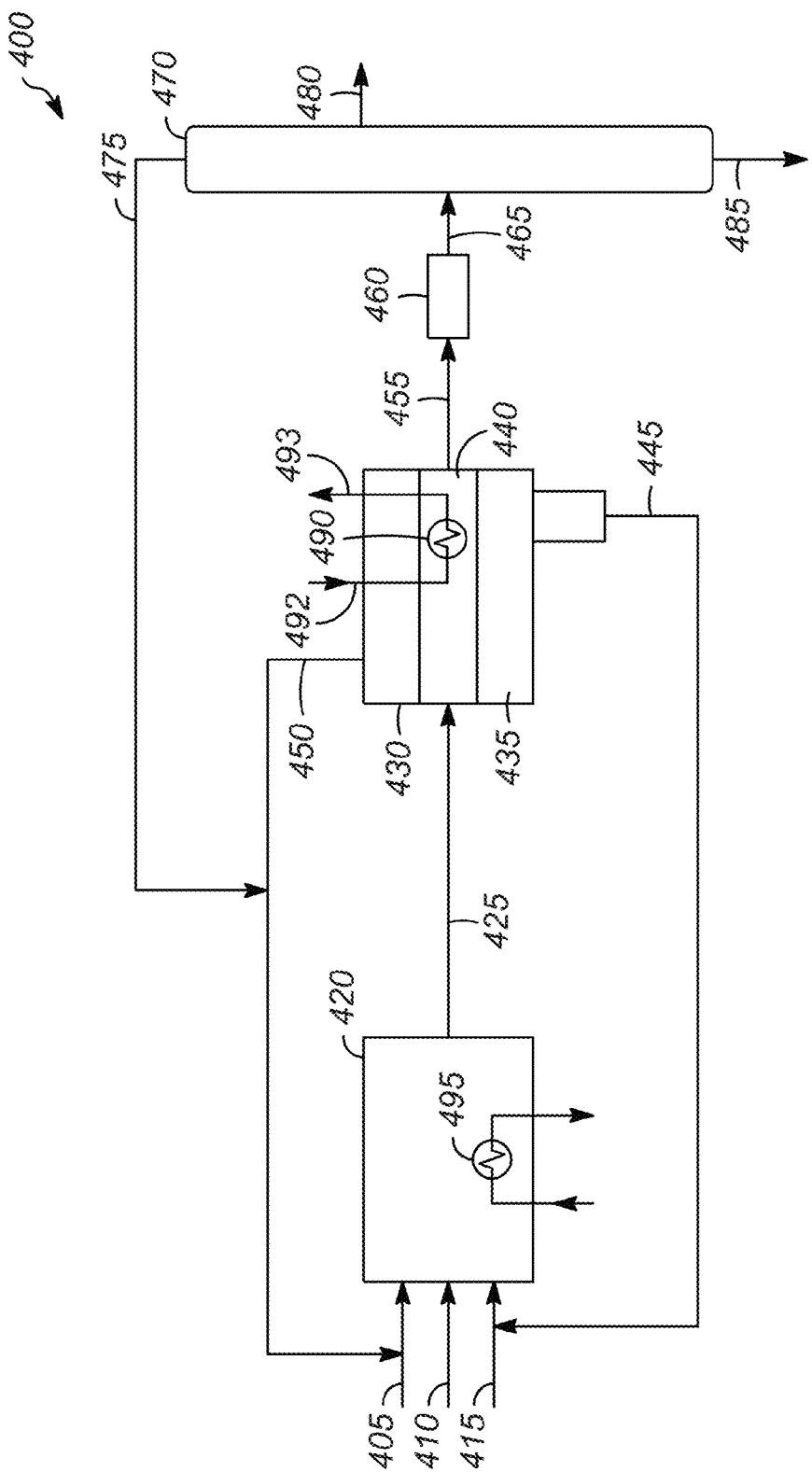
FIG. 4 illustrates yet another embodiment of a method for recovering entrained ionic liquid from an ionic liquid immiscible phase containing droplets of ionic liquid.

FIG. 4 illustrates another embodiment of the process 400. Rather than the ionic liquid droplet recovery occurring in a fractionation column, here the recovery takes place in a flash vessel.

A hydrocarbon feed 405, an olefin feed 410, and an ionic liquid catalyst 415 are fed into an alkylation reaction zone 420. The effluent 425 is fed to a flash vessel 430 which is operated at a pressure between the bubble points of n-butane and isobutane. Isobutane and some n-butane vaporizes upon entering the flash vessel 430. The remaining liquids separate by gravity into an ionic liquid phase 435 and a hydrocarbon phase 440 containing alkylate, n-butane, and the remaining isobutane. In order to prevent vaporization of alkylate, only about 10-30% of the isobutane can be vaporized. If a higher fraction is vaporized, the vapors will need to be separated by distillation because they will contain light portions of the alkylate product.

Due to the evaporation of the isobutane, there is a higher ionic liquid/hydrocarbon volume fraction in the flash vessel 430 compared to that in the first gravity separation zones in FIGS. 1-3. Thus, a larger portion of the ionic liquid settles by gravity in this configuration compared to the gravity first separation zones in FIGS. 1-3. A stream 445 of the ionic liquid can be recycled to the alkylation reaction zone 420.

A stream 450 of the isobutane vapor is compressed and recycled to the alkylation reaction zone 420.

A stream 455 of the liquid hydrocarbon phase 440 containing alkylate, the remaining isobutane, and n-butane is optionally treated in treater 460 to remove any remaining ionic liquid (or sent to a secondary separation zone to recover the remaining ionic liquid, not shown).

The treated stream 465 is fed to a fractionation column 470 where it is separated into an overhead stream 475 comprising isobutane, a side draw stream 480 of n-butane, and a bottoms stream 485 of alkylate. The overhead stream 475 comprising the isobutane can be condensed and recycled to the alkylation reaction zone 420. The non-condensable portion containing light ends, and HCl can be sent for further processing, such as to a stabilizer and/or a scrubber. The isobutane can be condensed, and recycled to the alkylation reaction zone 420.

The flash vessel 430 may contain a heat exchanger 490. The vaporization of the isobutane in flash vessel 430 will cool the refrigerant fluid 492 in heat exchanger 490. The cooled refrigerant fluid 493 can then be used to cool the alkylation reaction zone 420 using heat exchanger 495, or elsewhere.

This scheme has several advantages. It requires less equipment than the processes shown in FIGS. 1-3. In addition, it does not expose the ionic liquid to high temperatures in a column reboiler which may cause degradation. Feeding ionic liquid-free hydrocarbon to the column(s) also prevents possible corrosion of the column(s). Compared to FIGS. 1-3, this scheme will allow for a 10-30% smaller fractionation column because 30% of the isobutane is evaporated before the column. The disadvantage of this approach compared to that of FIGS. 1-3 is that a flash vessel does not allow for as precise control of the separation as a distillation column does.

Figure 5:
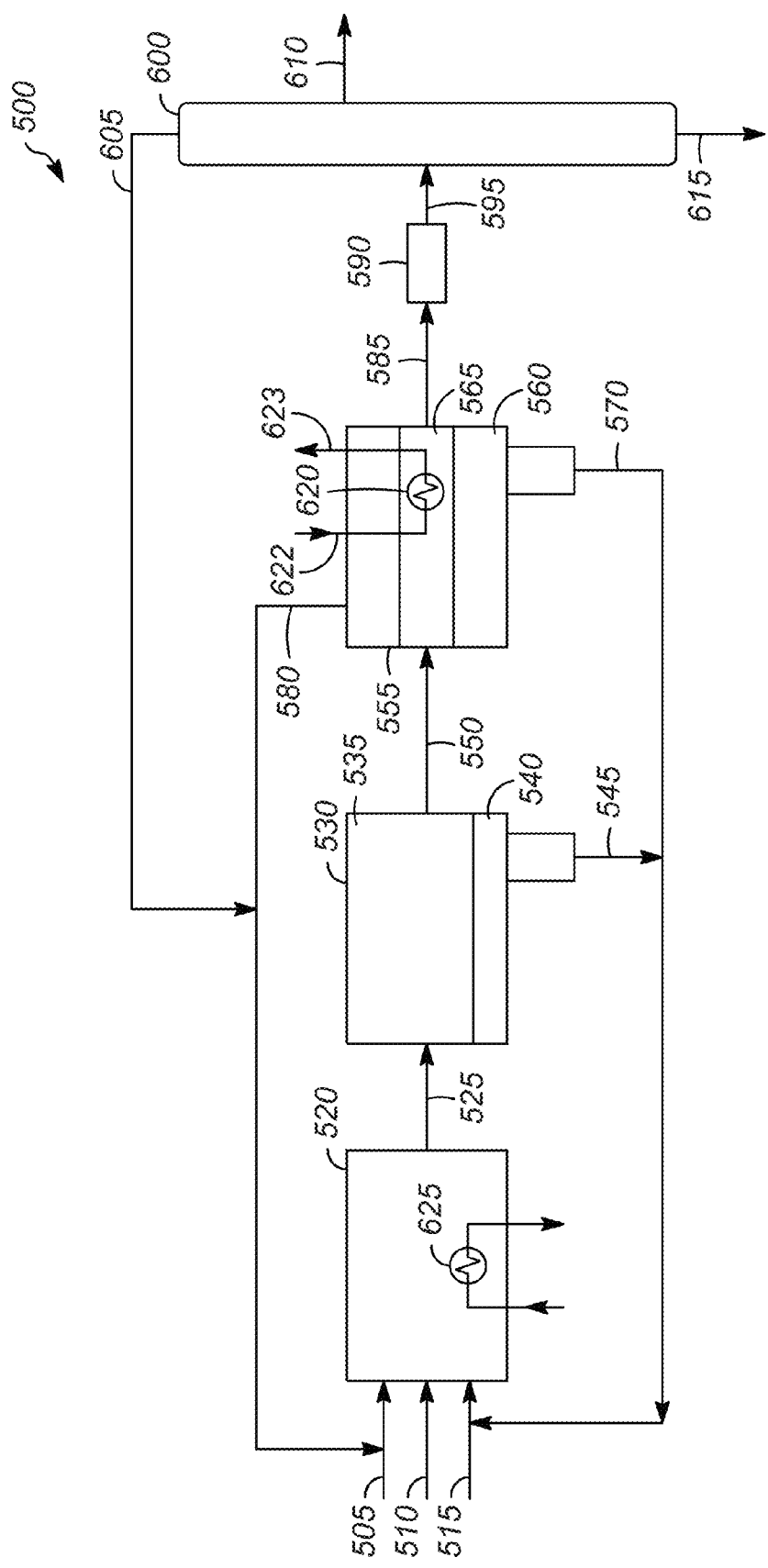
FIG. 5 illustrates another embodiment of a method for recovering entrained ionic liquid from an ionic liquid immiscible phase containing droplets of ionic liquid.

FIG. 5 illustrates a variation 500 of the process shown in FIG. 4. It includes a gravity separation zone before the flash vessel.

A hydrocarbon feed 505, an olefin feed 510, and an ionic liquid catalyst 515 are fed into an alkylation reaction zone 520. The effluent 525 is fed to a gravity separation zone 530 where it is separated into a hydrocarbon phase 535 and ionic liquid phase 540. A stream 545 of the ionic liquid phase 540 can be recycled to the alkylation reaction zone 520.

A stream 550 of the hydrocarbon phase, which contains isobutane, n-butane, alkylate, and ionic liquid droplets, is sent to the flash vessel 555. Isobutane and some n-butane vaporizes upon entering the flash vessel 555, and the remaining liquids separate by gravity into an ionic liquid phase 560 and a hydrocarbon phase 565 containing alkylate, n-butane, and the remaining isobutane.

A stream 570 of the ionic liquid can be recycled to the alkylation reaction zone 520.

A stream 580 of the isobutane vapor is compressed and recycled to the alkylation reaction zone 520.

A stream 585 of the liquid hydrocarbon phase 565 containing alkylate, the remaining isobutane, and n-butane is treated in treater 590 to remove any remaining ionic liquid.

The treated stream 595 is fed to a fractionation column 600 where it is separated into an overhead stream 605 comprising isobutane, a side draw stream 610 of n-butane, and a bottoms stream 615 of alkylate. The overhead stream 605 of isobutane can be condensed and recycled to the alkylation reaction zone 520.

The flash vessel 555 may contain a heat exchanger 620. The vaporization of the isobutane in flash vessel 555 will cool the refrigerant fluid 622 in heat exchanger 620. The cooled refrigerant fluid 623 can then be used to cool the alkylation reaction zone 520 using heat exchanger 625.

This configuration may be necessary for particular ionic liquid/hydrocarbon emulsions which are difficult to separate by gravity after the ionic liquid/hydrocarbon ratio has increased (which may occur because the buoyancy of hydrocarbon droplets in ionic liquid is impeded by the high viscosity of ionic liquid).

As used herein, the term about means within 10% of the value, or within 5%, or within 1%.

Example

Figure 6:
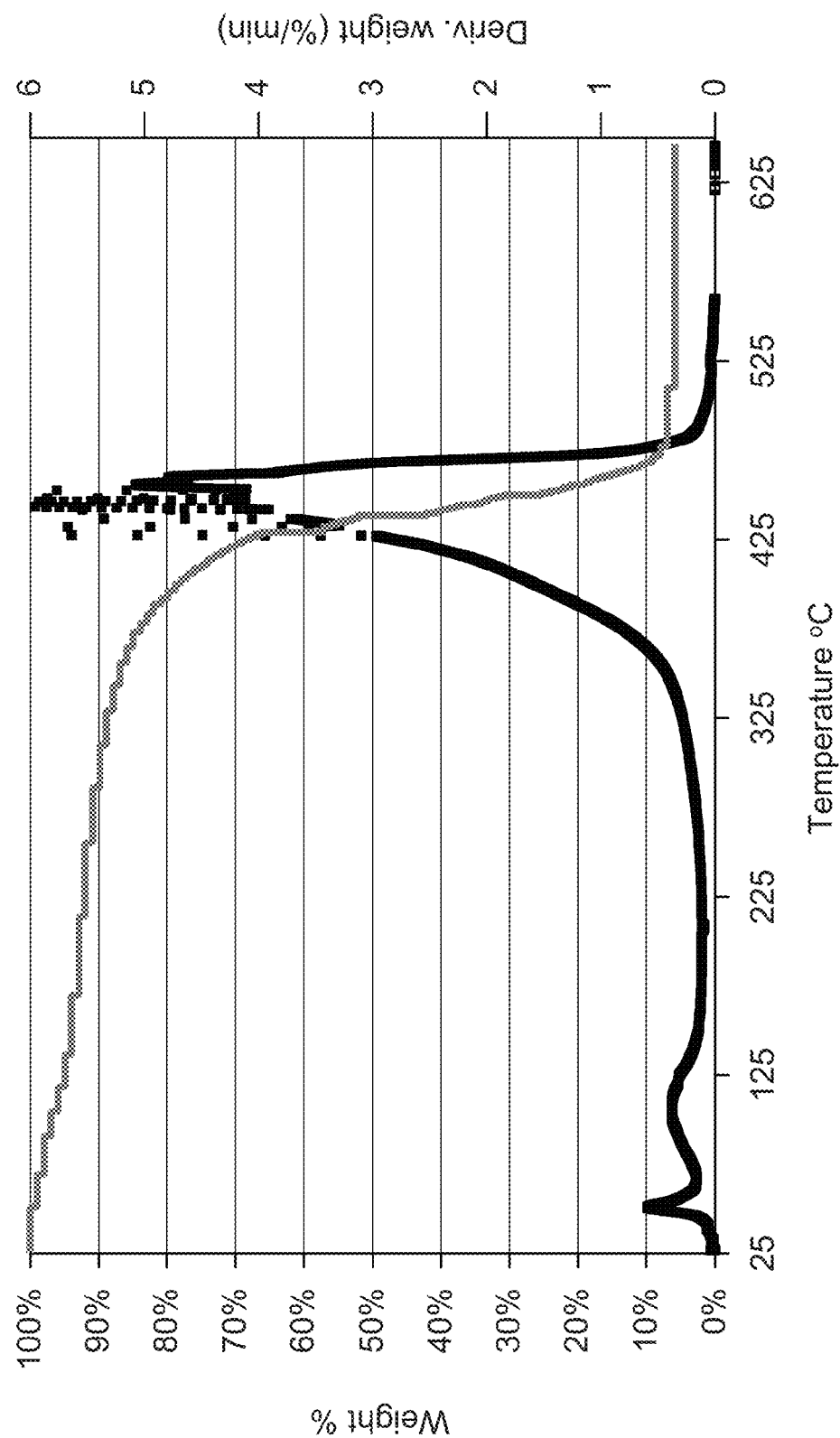
FIG. 6 is the thermogravimetric analysis of tributylhexylphosphonium heptachloroaluminate.

To demonstrate thermal stability of an ionic liquid active for alkylation, tributylhexylphosphonium-$Al_2Cl_7$, was analyzed by thermogravimetric analysis. The temperature was ramped from 25° C. to 650° C. in flowing helium at 5° C./min. FIG. 6 shows the resulting change in weight as a function of temperature (left axis), as well as the time derivative curve (right axis) which is an indication of temperature at which mass was lost. There is mass loss at approximately 70° C. to 150° C. which mass spectrometry shows is only HCl loss, which could easily be replaced in a reactivation step. Decomposition of the ionic liquid does not begin to occur until the temperature reaches approximately 260° C. The ionic liquid could be stable in a distillation column at temperatures below that value, and may be stable above that temperature for short periods of time.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method of recovering ionic liquid from a process stream comprising:
    separating the process stream comprising a mixture of hydrocarbons and ionic liquid into an ionic liquid phase and a hydrocarbon phase in a gravity separation zone, the hydrocarbon phase containing droplets of ionic liquid, and the hydrocarbon phase having a first volume fraction of ionic liquid;
    fractionating the hydrocarbon phase into at least two hydrocarbon fractions, at least one of the hydrocarbon fractions containing the droplets of ionic liquid, the fraction containing the droplets of ionic liquid having a second volume fraction of ionic liquid, the second volume fraction being greater than the first volume fraction; and
    separating at least a portion of the hydrocarbon fraction containing the droplets of ionic liquid in a second separation zone into an ionic liquid stream and at least one hydrocarbon stream.

2. The method of claim 1:
    wherein fractionating the hydrocarbon phase into the at least two hydrocarbon fractions comprises fractionating the hydrocarbon phase into at least a first hydrocarbon fraction, a second hydrocarbon fraction, and a third hydrocarbon fraction containing the droplets of ionic liquid; and
    wherein separating the at least the portion of the hydrocarbon fraction containing the droplets of ionic liquid in the second separation zone comprises separating the third hydrocarbon fraction into the ionic liquid stream and a second stream.

3. The method of claim 2 wherein at least a portion of the first hydrocarbon fraction is recycled to a reaction zone.

4. The method of claim 2 wherein the first hydrocarbon fraction comprises isobutane, the second hydrocarbon fraction comprises n-butane, and wherein the third hydrocarbon fraction comprises alkylate.

5. The method of claim 1:
    wherein fractionating the hydrocarbon phase into the at least two hydrocarbon fractions comprises fractionating the hydrocarbon phase into at least a first hydrocarbon fraction, and a second hydrocarbon fraction containing the droplets of ionic liquid in a first fractionation zone;

wherein separating the at least the portion of the hydrocarbon fraction containing the droplets of ionic liquid in the second separation zone comprises separating the second hydrocarbon fraction into the ionic liquid stream and a stream comprising at least two hydrocarbons; and further comprising:

fractionating the stream comprising the at least two hydrocarbons into a third fraction and a fourth fraction in a second fractionation zone.

6. The method of claim 5 wherein the first fractionation zone is operated at a pressure higher than a pressure of the second fractionation zone.

7. The method of claim 6 wherein the first fractionation zone is operated at a pressure in a range of about 965 kPa (g) (140 psig) to about 1310 kPa (g) (190 psig), and the second fractionation zone is operated at a pressure in a range of about 620 kPa (g) (90 psig) to about 965 kPa (g) (140 psig).

8. The method of claim 5 wherein the first hydrocarbon fraction comprises isobutane, the second hydrocarbon fraction comprises n-butane and alkylate, and wherein the third fraction comprises n-butane and the fourth fraction comprises alkylate.

9. The method of claim 5 wherein at least a portion of the first hydrocarbon fraction is recycled to a reaction zone.

10. The method of claim 1:
wherein fractionating the hydrocarbon phase into the at least two hydrocarbon fractions comprises:
fractionating the hydrocarbon phase into at least a first hydrocarbon fraction and a second hydrocarbon fraction containing the droplets of ionic liquid in a first fractionation zone; and
fractionating the second hydrocarbon fraction containing the droplets of ionic liquid into at least a third fraction and a fourth fraction containing the droplets of ionic liquid in a second fractionation zone; and
wherein separating the at least the portion of the hydrocarbon fraction containing the droplets of ionic liquid in the second separation zone comprises separating the fourth fraction into the ionic liquid stream and the at least one hydrocarbon stream.

11. The method of claim 10 wherein the first fractionation zone is operated at a pressure higher than the second fractionation zone.

12. The method of claim 11 wherein the first fractionation zone is operated at a pressure in a range of about 965 kPa (g) (140 psig) to about 1310 kPa (g) (190 psig), and the second fractionation zone is operated at a pressure in a range of about 620 kPa (g) (90 psig) to about 965 kPa (g) (140 psig).

13. The method of claim 10 wherein at least a portion of the first hydrocarbon fraction is recycled to a reaction zone.

14. The method of claim 1 further comprising:
treating the at least one hydrocarbon stream to remove residual ionic liquid.

15. The method of claim 1 further comprising:
recycling at least one of the ionic liquid phase and the ionic liquid stream to a process zone.

16. A method of recovering ionic liquid from a process stream comprising:
flashing at least a portion of the process stream comprising a mixture of hydrocarbons and ionic liquid into a vapor phase comprising a first portion of at least one first hydrocarbon and a liquid phase comprising a second portion of the at least one first hydrocarbon, at least one second hydrocarbon, and the ionic liquid, and separating the liquid phase into an ionic liquid phase and a hydrocarbon phase in a flash vessel, wherein the flash vessel is at a pressure between a bubble point of the at least one first hydrocarbon and a bubble point of the at least one second hydrocarbon; and
fractionating the hydrocarbon phase into at least two fractions.

17. The method of claim 16 wherein the process stream is separated into an ionic liquid stream and a hydrocarbon stream in a gravity separation zone before flashing the at least the portion of the process stream in the flash vessel, and wherein flashing the at least the portion of the process stream comprises flashing the at least a portion of the hydrocarbon stream.

18. The method of claim 16 further comprising:
treating the at least a portion of the hydrocarbon phase to remove residual ionic liquid before fractionating the hydrocarbon phase.

19. The method of claim 16 further comprising:
recycling at least a portion of the ionic liquid phase to a process zone.

20. The method of claim 16 further comprising:
condensing at least one of a portion of the vapor phase and a portion of the first fraction; and
recycling at least one of the portion of the condensed vapor phase and the portion of the condensed first fraction to a process zone.

* * * * *